United States Patent [19]

Machinami et al.

[11] Patent Number: 5,294,629
[45] Date of Patent: Mar. 15, 1994

[54] BENZOTHIAZOLE AND BENZIMIDAZOLE DERIVATIVES AND ANTIULCER AGENT CONTAINING THE SAME

[75] Inventors: Tomoya Machinami; Kazue Yasufuku; Seiji Shibahara; Fumiya Hirano; Yasukatsu Yuda; Motohiro Nishio; Yuji Matsuhashi; Takashi Tsuruoka; Kiyoaki Katano; Shigeharu Inoye, all of Kanagawa, Japan

[73] Assignee: Meiji Seika Kaisha, Ltd., Tokyo, Japan

[21] Appl. No.: 37,671

[22] Filed: Mar. 25, 1993

Related U.S. Application Data

[63] Continuation of Ser. No. 799,023, Nov. 25, 1991, abandoned, which is a continuation of Ser. No. 440,067, Nov. 22, 1989, abandoned.

[30] Foreign Application Priority Data

Nov. 22, 1988 [JP] Japan .................. 63-293689
May 10, 1989 [JP] Japan .................. 1-115184

[51] Int. Cl.$^5$ ................. C07D 235/28; C07D 277/76; A61K 31/415; A61K 31/425
[52] U.S. Cl. ............................ 514/366; 514/395; 548/166; 548/169; 548/307.1
[58] Field of Search .............. 548/166, 307.1; 514/366, 395

[56] References Cited

U.S. PATENT DOCUMENTS

| | | | |
|---|---|---|---|
| 2,018,813 | 10/1935 | Schubert | 548/166 |
| 2,040,467 | 5/1936 | Clifford | 548/169 |
| 2,070,523 | 2/1937 | Clifford | 548/169 |
| 2,498,617 | 2/1950 | Gluesenkamp | 548/169 |
| 3,480,643 | 11/1969 | Lutz et al. | 260/309.2 |
| 4,287,349 | 9/1981 | Fields | 548/166 |
| 4,873,346 | 10/1989 | Anderson | 548/169 |

FOREIGN PATENT DOCUMENTS

| | | |
|---|---|---|
| 0045200 | 2/1982 | European Pat. Off. . |
| 0174717 | 3/1986 | European Pat. Off. . |
| 268956 | 6/1988 | European Pat. Off. .......... 548/169 |
| 8705021 | 8/1987 | PCT Int'l Appl. . |
| 0416291 | 9/1934 | United Kingdom . |

OTHER PUBLICATIONS

Ignatov, Izv. Vyssh Uchebn Zaved Khim Khim Tekhnol 22 1007 (1979).

Priilezharva, Zh. Org. K Him. 2 (10) 1883 (1966) Abstract.

J. Med. Chem., 31, pp. 1778–1785, Sanfilippo, et al, "Synthesis of (Aryloxy) alkylamines ... " (1988).

Chemical Abstracts, vol. 71, No. 17, Oct. 27, 1969, p. 393, Abstract No. 81252z, S. V. Zhuravlev et al, "Synthesis of 2–mercaptobenzothiozole derivatives".

(List continued on next page.)

Primary Examiner—Robert Gerstl
Attorney, Agent, or Firm—Sughrue, Mion, Zinn, Macpeak & Seas

[57] ABSTRACT

A novel benzothiazole or benzimidazole derivative represented by formula (I)

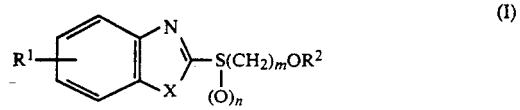

wherein X represents a sulfur atom or a NH group; $R^1$ represents a hydrogen atom, a lower alkoxy group, a chlorine atom, a bromine atom or an iodine atom; $R^2$ represents a hydrogen atom a substituted or unsubstituted lower alkyl group, a vinyl group, an aryl group or an acyl group; m is an integer of 1, 2 or 3; and n is an integer of 0, 1 or 2, which shows an excellent acid secretion suppressing effect and gastric mucosa protecting effect, and an antiulcer agent containing the same as an active ingredient.

7 Claims, No Drawings

OTHER PUBLICATIONS

Synthesis, Journ. of Synthetic Organic Synthesis, No. 3, Mar. 1988, pp. 159-262, P. Brownbridge et al, "One—Pot synthesis of sulphinic esters from disulphides", pp. 252-254.

Chemical Abstracts, vol. 69, No. 11, Sep. 9, 1968; pp. 324-325, Abstract No. 47349f, E. A. Kuznetsova et al, "Synthesis of thiazolino[3,2-a-]benzimidazole and some of its derivatives".

Chemical Abstracts, vol. 58, No. 9, Apr. 29, 1963, pp. 9043-9044, Abstract No. 9044a, E. A. Kuznetsova, "Synthesis and properties of 2-mercaptobenzothiozole derivatives."

Chemical Abstracts, vol. 92, p. 667, Abstract No. 92:76380u, V. A. Ignatov et al, "Study of the Reaction by bis(2-benzothiazolyl)disulfide with amines" (1980).

Chemical Abstracts, vol. 66, p. 5236, Abstract No. 55430h, E. N. Prilezhaeva et al, "Synthesis based on 2-benzothiazolyl vinyl sulfied"(1968).

BENZOTHIAZOLE AND BENZIMIDAZOLE DERIVATIVES AND ANTIULCER AGENT CONTAINING THE SAME

This is a continuation of application Ser. No. 07/799,023, filed No. 25, 1991, which is a continuation of application Ser. No. 07/440,067, filed Nov. 22, 1989, both now abandoned.

FIELD OF THE INVENTION

This invention relates to a novel benzothiazole or benzimidazole derivative having an antiulcer activity, and to an antiulcer agent containing the derivative as an active ingredient which is effective for preventing and/or treating gastric ulcer and duodenal ulcer.

BACKGROUND OF THE INVENTION

It is desired to provide an antiulcer agent which exerts effects on suppression of acid secretion as well as protection of gastric mucosa. Known drugs capable of suppressing acid secretion include histamine $H_2$ receptor blocking drugs such as cimetidine. However, these drugs show no effect on protection of gastric mucosa. Furthermore, they are accompanied by some undesirable side effects on, for example, the central nervous system, which makes them insufficient to be used in preventing or treating ulcer.

Recently, it is known that benzimidazole derivatives such as omeprazole have an intense $H^+$, $K^+$ATPase-inhibitory activity and thus, considerably suppress acid secretion, which would sometimes induce anacidity. Further, these compounds are disadvantageous in that they are unstable to acids and thus frequently decomposed by gastric acid.

Accordingly, it has been urgently required to develop an antiulcer agent which shows well-balanced effects on both suppression of acid secretion and protection of gastric mucosa and has a low toxicity, and is effective for various ulcers and stable against gastric acid.

On the other hand, it is reported that some benzothiazole compounds have $H^+$, $K^+$ATPase-inhibitory and acid secretion-suppressing activities [cf. J. Med. Chem., 31, 1778 (1778 (1988)]. However, the effectiveness of these compounds on various ulcer models have never been reported.

SUMMARY OF THE INVENTION

An object of the present invention is to provide an antiulcer agent having well-balanced effects on suppressing acid secretion and protecting gastric mucosa, having a low toxicity, effective in preventing or treating various ulcers.

In order to solve the above-mentioned problems, the present inventors have conducted extensive studies. As a result, the present inventors have found out that a specific benzothiazole derivative or a specific benzimidazole derivative shows an intense effect on suppression of acid secretion as well as on protection of gastric mucosa and that they have an antiulcer activity on various ulcer models.

The present invention provides a novel benzothiazole derivative or a novel benzimidazole derivative represented by formula (I):

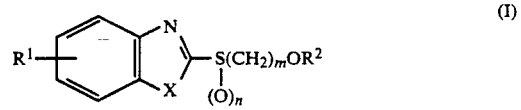

wherein X represents a sulfur atom or a NH group; $R^1$ represents a hydrogen atom, a lower alkoxy group, a chlorine atom, a bromine atom or an iodine atom; $R^2$ represents a hydrogen atom, a substituted or unsubstituted lower alkyl group, a vinyl group, an aryl group or an acyl group $R^1$ and $R^2$ do not simultaneously represent a hydrogen atom; m is an integer of 1, 2 or 3; and n is an integer of 0, 1 or 2.

The present invention also provides an antiulcer agent containing an antiulcer effective amount of the compound of formula (I) as an active ingredient which is useful for preventing and/or treating gastric ulcer and duodenal ulcer.

DETAILED DESCRIPTION OF THE INVENTION

The alkyl moiety of the alkoxy group represented by $R^1$ and lower alkyl group represented by $R^2$ has 1 to 4 carbon atoms such as methyl, ethyl, n-propyl, isopropyl or n-butyl. The lower alkyl group represented by $R^2$ may be substituted with a halogen atom, a hydroxy group, an alkoxy group, a hydroxyalkoxy group or an aryl group, preferably an alkoxy group such as methoxy, ethoxy or n-propoxy and an aryl group such as phenyl or p-methoxyphenyl.

Among the compounds of formula (I) according to the present invention, a compound represented by formula (Ia):

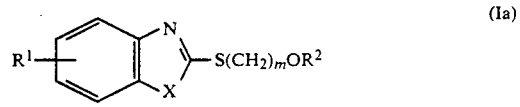

wherein X, $R^1$, $R^2$ and m are as defined above; can be obtained by the following process A or B.

Process A:

A compound represented by formula (II):

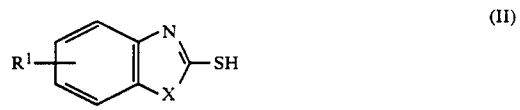

wherein X and $R^1$ are as defined above;
is allowed to react with a compound represented by formula (III):

$$Y(CH_2)_mOR^2 \quad \text{(III)}$$

wherein $R^2$ and m are as defined above; and Y represents a halogen atom, a tosyloxy group, a trifluoromethanesulfonyloxy group or a mesyloxy group;
in a solvent inert to the reaction such as N,N-dimethylformamide in the presence of a base such as a metal hydride, preferably sodium hydride, or sodium hydroxide to give the compound of formula (Ia).

The reaction is carried out at a temperature ranging from $-20°$ to $150°$ C., preferably $20°$ to $100°$ C., for 0.5 to 24 hours. The compound of formula (III) is used in an amount of 1 to 3 molar equivalent, preferably 1.1 to 2 molar equivalent, of the compound of formula (II).

Process B:

A compound represented by formula (IV):

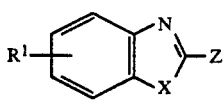

wherein R¹ is as defined above; and Z represents a halogen atom;
is allowed to react with a compound represented by formula (V):

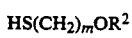

wherein R² and m are as defined above;
in a solvent inert to the reaction such as N,N-dimethylformamide in the presence of a base such as a metal hydride, preferably sodium hydride, or a metal hydroxide, preferably sodium hydroxide, to give the compound of formula (Ia).

The reaction is carried out at a temperature ranging from −20° to 150° C., preferably 20° to 100° C., for 0.5 to 24 hours. The compound of formula (V) is used in an amount of 1 to 3 molar equivalent, preferably 1.1 to 2 molar equivalent of the compound of formula (IV).

Then, the compound of formula (Ia) is treated with 1 to 1.2 molar equivalent of an oxidizing agent in a solvent inert to the reaction to give a sulfoxide compound of formula (Ib):

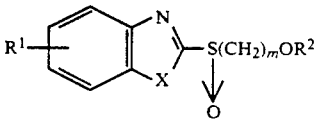

wherein X, R¹, R² and m are as defined above;
as a major product. When additional 1 to 1.5 molar equivalent of the oxidizing agent is used in this oxidation reaction, a sulfone compound represented by formula (Ic):

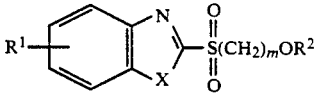

wherein X, R¹, R² and m are as defined above;
can be obtained as a major product.

Examples of the oxidizing agent to be used in this reaction include hydrogen peroxide, peracid derivatives such as m-chloroperbenzoic acid and sodium periodate, manganese dioxide, tert-butyl hydroperoxide and N-bromosuccinimide.

Examples of the solvent include those commonly employed such as water, acetic acid, alkyl halides such as methylene chloride and ketones such as acetone. It is preferable to conduct the above oxidation in acetic acid in the presence of sodium tungstate using hydrogen peroxide; or in methylene chloride using m-chloroperbenzoic acid.

The oxidation reaction is carried out at a temperature ranging from −20° to 100° C., preferably 0 to 30° C, for 0.5 to 24 hours.

The thus-obtained compound of formula (I) can be isolated and purified in a conventional manner such as crystallization, precipitation or column chromatography.

The effects of the compound of the present invention is described in detail with reference to the following pharmacological tests.

1. Submerged restraint stress ulcer test

A test compound as shown in Table 1 was suspended in 0.5% carboxymethylcellulose (CMC) and orally administered once to male Wister rats aged 11 weeks, which had been fasted for 18 hours, at a dose of 30 mg/5 ml/kg body weight. Similarly, 5 ml of 0.5% CMC was administered to a control group. One hour after the administration of the test compound, the rats were kept in restraining gages and immersed in water at 20 to 22° C up to the chest. Then, these animals were allowed to stand as such for six hours so as to load a stress. After pulling up from the water, each animal was sacrificed by vertebral cervical dislocation and the stomach was taken out. 5 ml of a 5% aqueous solution of formaldehyde was injected into the stomach and the stomach was immersed in said solution for 30 minutes for fixation. The specimen thus fixed was cut along the curvatura ventriculi major and the major axis of the formed ulcer was measured with a slide calipers (mm). The sum of the major axes of the total ulcers was made an ulcer index.

The ulceration inhibitory ratio was calculated according to the following equation:

Ulceration inhibitory ratio (%) =

$$\left(1 - \frac{\text{Average ulcer index of test group}}{\text{Average ulcer index of control group}}\right) \times 100$$

The results are shown in Table 1.

TABLE 1

| Test compound Example No. | Ulceration inhibitory ratio (%) |
|---|---|
| 1 | 57.0** |
| 2 | 93.0* |
| 3 | 35.3 |
| 4 | 59.9** |
| 9 | 58.5** |
| 11 | 63.5** |
| 17 | 73.6** |
| comparison (omeprazole) | 99.0 |

Note:
*p < 0.05.
**p < 0.01.

2. Histamine-induced ulcer test

A compound obtained in Example 2 was suspended in 0.5% CMC and orally administered once to male Donryu rats, which had been fasted for 24 hours, at a dose of 30 mg/5 ml/kg. Similarly, 5 ml of 0.5% CMC was administered to a control group. One hour after the administration of the test compound, a solution of histamine dihydrochloride in a physiological saline solution was intraperitoneally administered to the rats at a dose of 200 mg/5 ml/kg. After five hours, each animal was sacrificed and the stomach was taken out and treated with an aqueous solution of formaldehyde to determine the ulceration inhibitory ratio in the same manner as in the above-described submerged restrain stress ulcer test. As a result, the ulceration inhibitory ratio was 50%.

3. Aspirin-induced ulcer test

A test compound suspended in 0.5% carboxymethylcellulose orally administered to male Donryu rats, which had been fasted for 24 hours, at a dose of 30 mg/5 ml/kg body weight. Similarly, 5 ml of 0.5% CMC was administered to a control group. One hour after the administration of the test compound, Aspirin suspended in 0.5% CMC was orally administered to the rats at a dose of 300 mg/5 ml/kg body weight. After four hours, each animal was sacrificed and the stomach was taken out and treated with an aqueous solution of formaldehyde to determine the ulceration inhibitory ratio in the same manner as in the submerged restrain stress ulcer test.

TABLE 2

| Test compound | Ulceration inhibitory ratio (%) |
| --- | --- |
| 1 | 21.3 |
| 2 | 85* |

Note:
*$p < 0.05$.

4. Ethanol-induced ulcer test

A compound obtained in Example 2 was suspended in 0.5% CMC and orally administered to male Donryu rats, which had been fasted for 48 hours and abstained from water for 24 hours, at a dose of 5 ml/kg body weight. Similarly, 5 ml of 0.5% CMC was administered to a control group. One hour after the administration of the test compound, 100% ethanol was orally administered to the rats at a dose of 5 ml/kg body weight. After one hour, each animal was sacrificed and the stomach was taken out and treated in the above-mentioned manner. Then, erosion formation in the stomach was observed.

As a result, in a control group to which 0.5% CMC was given alone, erosion was formed at a frequency of almost 100%. In contrast thereto, in a test group to which the test compound was administered at a dose of 50 mg/5 ml/kg body weight, erosion formation was inhibited at a frequency of almost 100%.

5. Acute toxicity

A compound prepared in Example 2 was suspended in 0.5% CMC to give a predetermined concentration. Then, three male ICR mice aged 5 weeks were forced to orally take the above suspension once. After observing these animals for seven days, no animal died at a dose of 1,000 mg/10 ml/kg body weight.

The compound of formula (I) of the present invention may be administered alone. Alternately, it may be blended with other conventional pharmacologically acceptable carriers, excipients or diluents and formulated into a desired form suitable for oral or parenteral administration. In the former case, the compound of formula (I) may be generally administered to an adult at a dose of 50 to 500 mg once or several times per day. In case of parenteral administration, the compound of formula (I) may be formulated into an aqueous solution for injection or suppository with a pharmacologically acceptable water soluble salt to give a concentration of 0.5 to 10% by weight. The compound of formula (I) may be administered intravenously or intrarectally to an adult at a dose of 0.5 to 10 mg once or several times per day.

The compound of formula (I) according to the present invention shows a inhibitory effect on various ulcer models. Thus it is useful as a remedy for peptic ulcer.

To further illustrate the present invention, the following Examples are given, though the scope of the present invention is not restricted thereto. In Examples, the procedure was conducted at room temperature unless otherwise specified.

EXAMPLE 1

5-Chloro-2-[(2-ethoxyethyl)thio]benzothiazole 5.00 g (24.8 mmol) of 5-chloro-2-mercaptobenzothiazole was dissolved in 25 ml of N,N-dimethylformamide. 710 mg (29.6 mmol) of sodium hydride was added to the above solution and the mixture was stirred for one hour. Then, 5.44 ml (49.6 mmol) of 2-chloroethyl ethyl ether was added to the resulting suspension. and the mixture was stirred for two hours while heating at 50° C. The reaction mixture was diluted with 500 ml of chloroform and 500 ml of 20% aqueous solution of sodium chloride was added thereto. After shaking and washing the mixture, the chloroform layer was separated, dried over anhydrous magnesium sulfate and concentrated under reduced pressure. The residue thus obtained was separated and purified by silica gel chromatography using a solution of hexane/ethyl acetate (10/1 by volume) as a developing solvent. Thus, 5.40 g of the desired compound was obtained in the form of a colorless oily substance. Yield: 80%.

EXAMPLE 2

5-Chloro-2-[(2-ethoxyethyl)sulfinyl]benzothiazole 2.00 g (7.3 mmol) of the compound obtained in the above Example 1 was dissolved in 10 ml of acetic acid. To this solution, were added 0.99 ml (8.74 mmol) of 30% aqueous solution of hydrogen peroxide and a catalytic amount of sodium tungstate successively. The reaction mixture was stirred for one hour. Then, the mixture was poured into 200 ml of 20% aqueous solution of sodium chloride and the resulting mixture was neutralized with sodium hydrogencarbonate. Next, it was extracted with 200 ml of chloroform. The chloroform layer was separated, dried over anhydrous magnesium sulfate and concentrated under reduced pressure. The residue thus obtained was purified by silica gel chromatography using a solution of hexane/ethyl acetate (10/1 by volume) as a developing solvent and recrystallized from ethanol. Thus, 1.47 g of the desired compound showing a m.p. of 96° to 97° C. was obtained in the form of crystals. Yield: 69%.

EXAMPLE 3

5-Chloro-2-[(2-ethoxyethyl)sulfonyl]benzothiazole 89 mg (0.33 mmol) of the compound obtained in Example 1 was dissolved in 1 ml of acetic acid. To this solution, were added 0.094 ml (0.83 mmol) of a 30% aqueous solution of hydrogen peroxide and a catalytic amount of sodium tungstate successively. The resulting mixture was allowed to react for 12 hours. Then, it was treated in the same manner as in Example 2 to give 80 mg of the desired compound. Yield: 80.5%.

Further, compounds of the following Examples 4 to 22 were synthesized by the same method as either of those described in Examples 1 to 3. The physicochemical properties of these compounds are shown in Table 3.

EXAMPLE 4
2-[(2-Ethoxyethyl)sulfinyl]benzothiazole

EXAMPLE 5
2-[(2-Ethoxyethyl)thio]-6-ethoxybenzothiazole

EXAMPLE 6
2-[(2-Ethoxyethyl)sulfinyl]-6-ethoxybenzothiazole

EXAMPLE 7
2-[(2-Ethoxyethyl)sulfonyl]-6-benzothiazole

EXAMPLE 8
5-Chloro-2-[(2-hydroxyethyl)thio]benzothiazole

EXAMPLE 9
5-Chloro-2-[(2-hydroxyethyl)sulfinyl]benzothiazole

EXAMPLE 10
5-Chloro-2-[(2-(2-hydroxyethoxy)ethoxy}ethylthio]-benzothiazole

EXAMPLE 11
5-Chloro-2-[(2-(2-hydroxyethoxy)ethoxy}ethyl-sulfinyl]benzothiazole

EXAMPLE 12
5-Chloro-2-[(2-vinyloxyethyl)thio]benzothiazole

EXAMPLE 13
5-Chloro-2-[(2-vinyloxyethyl)sulfinyl]benzothiazole

EXAMPLE 14
2-[(2-Benzyloxyethyl)sulfinyl]-5-chlorobenzothiazole

EXAMPLE 15
5-Chloro-2-[(2-phenylacetoxyethyl)sulfinyl]benzothiazole

EXAMPLE 16
2-[(2-Ethoxyethyl)thio]benzimidazole

EXAMPLE 17
2-[(2-Ethoxyethyl)sulfinyl]benzimidazole

EXAMPLE 18
2-[(2-Ethoxyethyl)sulfonyl]benzimidazole

EXAMPLE 19
5-Chloro-2-[(3-ethoxypropyl)thio]benzothiazole

EXAMPLE 20
5-Chloro-2-[(3-ethoxypropyl)sulfinyl]benzothiazole

EXAMPLE 21
5-Chloro-2-[(3-methoxypropyl)thio]benzothiazole

EXAMPLE 22
5-Chloro-2-[(3-methoxypropyl)sulfinyl]benzothiazole

TABLE 2

$R^1$—[benzothiazole ring]—$S(CH_2)_mOR^2$, $X$, $(O)_n$

| Ex. No. | $R^1$ | X | m | n | $R^2$ | Mass spectrum (EI, m/z) | NMR spectrum (δ ppm, CDCl₃) |
|---|---|---|---|---|---|---|---|
| 1 | 5-Cl | S | 2 | 0 | $C_2H_5$ | 273 (M⁺), 201 | 1.22(3H, t), 3.4~3.85 (6H, m), 7.25(1H, dd), 7.59(1H, d), 7.84(1H, d) |
| 2 | 5-Cl | S | 2 | 1 | $C_2H_5$ | 289 (M⁺), 217, 169 | 1.08(3H, t), 3.2~3.65 (2H, m), 3.50(2H, q), 3.93 (2H, t), 7.47(1H, dd), 7.91(1H, d), 8.04(1H, d) |
| 3 | 5-Cl | S | 2 | 2 | $C_2H_5$ | 305 (M⁺), 260, 168 | 0.85(3H, t), 3.35(2H, dd) 3.6~4.0(4H, m), 7.53 (1H, dd), 7.92(1H, dd), 8.20(1H, dd) |
| 4 | H | S | 2 | 1 | $C_2H_5$ | 239 (M⁺), 167 | 1.10(3H, t), 3.4~3.6 (4H, m), 3.94(2H, t), 7.3~7.7(2H, m), 7.95~8.15(2H, m) |
| 5 | 6-$C_2H_5O$ | S | 2 | 0 | $C_2H_5$ | 283 (M⁺), 238, 210 | 1.21(3H, t), 1.43(3H, t) 3.4~3.9(6H, m), 4.06 (2H, q), 6.99(1H, dd), 7.21(1H, d), 7.73(1H, d) |
| 6 | 6-$C_2H_5O$ | S | 2 | 1 | $C_2H_5$ | 299 (M⁺), 226, 178 | 1.12(3H, t), 1.46(3H, t), 3.3~3.6(4H, m), 3.8~4.2 (4H, m), 7.13(1H, dd), 7.40(1H, d), 7.92(1H, d) |
| 7 | 6-$C_2H_5O$ | S | 2 | 2 | $C_2H_5$ | 315 (M⁺), 270, 178 | 0.90(3H, t), 1.47(3H, t), 3.37(2H, q), 3.6~4.3 (6H, m), 7.19(1H, dd), 7.36(1H, d), 8.06(1H, d) |
| 8 | 5-Cl | S | 2 | 0 | H | 245 (M⁺), 214, 200 | 3.46(1H, t), 3.51(2H, t) 4.02(2H, t), 7.27(1H, dd) 7.64(1H, d), 7.83(1H, d) |
| 9 | 5-Cl | S | 2 | 1 | H | 261 (M⁺), 244, 216, 168 | 2.58(1H, t), 3.2~3.8 (2H, m), 4.1~4.3(2H, m), 7.48(1H, dd), 7.93 (1H, d), 8.06(1H, d) |
| 10 | 5-Cl | S | 2 | 0 | $(CH_2)_2O(CH_2)_2OH$ | | 2.2~2.5(1H), 3.5~4.0 |

TABLE 2-continued $$R^1 \underset{X}{\overset{N}{\bigotimes}} S(CH_2)_m OR^2 \quad (O)_n$$

| Ex. No. | $R^1$ | X | m | n | $R^2$ | Mass spectrum (EI, m/z) | NMR spectrum ($\delta$ ppm, CDCl$_3$) |
|---|---|---|---|---|---|---|---|
| 11 | 5-Cl | S | 2 | 1 | (CH$_2$)$_2$O(CH$_2$)$_2$OH | 333 (M$^+$), 302, 228, 200, 349 (M$^+$), 318, 260, 216, 168 | (12H, m), 7.26(1H, dd), 7.64(1H, d), 7.83(1H, d) 2.4~2.7(1H), 3.34(12H, m) 7.46(1H, dd), 7.92(1H, d) 8.06(1H, d) |
| 12 | 5-Cl | S | 2 | 0 | —CH=CH$_2$ | 271 (M$^+$), 244, 228, 214, 200 | 3.64(2H, dt), 4.0~4.4 (4H, m), 6.48(1H, dd), 7.26(1H, dd), 7.64(1H, d) 7.84(1H, d) |
| 13 | 5-Cl | S | 2 | 1 | —CH=CH$_2$ | 287 (M$^+$) (FD) | 3.53(2H, dd), 4.0~4.3 (4H, m), 6.36(1H, dd), —7.47(1H, dd), 7.92(1H, d) 8.05(1H, d) |
| 14 | 5-Cl | S | 2 | 1 | —CH$_2$Ph | 351 (M$^+$), 274, 260, 230, 216, 168 | 3.50(2H, t), 4.00(2H, t), 4.51(2H, s), 7.23(5H, s) 7.42(1H, dd), 7.86(1H, d) 8.02(1H, d) |
| 15 | 5-Cl | S | 2 | 1 | —C(O)CH$_2$Ph | 379 (M$^+$), 244, 216, 168 | 3.43(2H, s), 3.4~3.8 (2H, m), 4.61(2H, t), 7.1~7.3(5H, m), 7.47 (1H, dd), 7.92(1H, d) 8.05(1H, d) |
| 16 | H | NH | 2 | 0 | C$_2$H$_5$ | 222 (M$^+$), 117 | 1.31(3H, t), 3.35(2H, t) 3.64(2H, q), 3.87(2H, t) 7.1~7.3(2H, m), 7.3~7.8 (2H, m) |
| 17 | H | NH | 2 | 1 | C$_2$H$_5$ | 238 (M$^+$), 165, 117 | 1.10 (3H, t), 3.4~3.7 (4H, m), 3.95(2H, t), 7.2~7.4(2H, m), 7.45~7.95(2H, m) |
| 18 | H | NH | 2 | 2 | C$_2$H$_5$ | 254 (M$^+$), 209, 181, 117 | 0.88(3H, t), 3.37(2H, q), 3.7~4.0(4H, m), 7.3~7.5 (2H, m), 7.7~7.8(2H, m) |
| 19 | 5-Cl | S | 3 | 0 | C$_2$H$_5$ | — | 1.22(3H, t), 2.10(2H, qui) 3.46(2H, q), 3.53(2H, t) 3.59(2H, t], 7.27(1H, dd) 7.66(1H, d), 7.84(1H, d) |
| 20 | 5-Cl | S | 3 | 1 | C$_2$H$_5$ | 303 (M$^+$) | 1.18(3H, t), 1.91~2.02(1H, m), 2.17~2.29(1H, m), 3.23~3.32(1H, m), 3.37~ 3.42(1H, m), 3.42~3.51 (2H,m), 3.51~3.62(2H, m), 7.49(1H, dd), 7.94(1H, d), 8.07(1H, d) |
| 21 | 5-Cl | S | 3 | 0 | CH$_3$ | 273 (M$^+$) | 2.11(2H, quint), 3.37 (3H, S), 3.44(2H, t), 3.53 (2H, t), 7.26(1H, dd), 7.64 (1H, d), 7.84(1H, d) |
| 22 | 5-Cl | S | 3 | 1 | CH$_3$ | 289 (M$^+$) | 1.90~2.00(1H, m), 2.19~ 2.29(1H, m), 3.21~3.31 (1H, m), 3.32(1H, S), 3.36~ 3.44(1H, m), 3.48~3.56 (2H, m), 7.48(1H, dd), 7.94 (1H, d), 8.03(1H, d) |

While the invention has been described in detail and with reference to specific embodiments thereof, it will be apparent to one skilled in the art that various changes and modifications can be made therein without departing from the spirit and scope thereof.

What is claimed is:

1. An antiulcer agent containing, as an active ingredient, a compound selected from the group consisting of 5-chloro-2-[(2-ethoxyethyl)sulfinyl]benzothiozole, 2-[(2-ethoxyethyl)-sulfinyl]benzothiozole, 5-chloro-2-[(2-hydroxyethyl)sulfinyl]-benzothiozole, 5-chloro-2-[2-{2-(2-hydroxyethoxy)ethoxy}ethylsulfinyl]benzothiozole and 2-[2-ethoxyethyl)sulfinyl]benzimidazole.

2. A method of preventing and/or treating peptic ulcer which comprises administering to a patient an antiulcer agent containing, as an active ingredient, a compound selected from the group consisting of 5-chloro-2-[(2-ethoxyethyl)sulfinyl]benzothiozole, 2-[(2-ethoxyethyl)sulfinyl]benzothiozole, 5-chloro-2-[(2-hydroxyethyl)sulfinyl]benzothiozole, 5-chloro-2-[2-{2-(2-hydroxyethoxy)ethoxy}ethylsulfinyl]benzothiozole and 2-[2-ethoxyethyl)sulfinyl]benzimidazole.

3. 5-Chloro-2-[(2-ethoxyethyl)sulfinyl]benzothiazole.

4. 2-[(2-Ethoxyethyl)sulfinyl]benzothiazole.

5. 5-Chloro-2-[(2-hydroxyethyl)sulfinyl]benzothiazole.

6. 5-Chloro-2-{2-(2-hydroxyethoxy)ethoxy}ethylsulfinyl]benzothiazole.

7. 2-[2-Ethoxyethyl)sulfinyl]benzimidazole.

* * * * *